United States Patent
Charles

(10) Patent No.: US 9,649,021 B1
(45) Date of Patent: May 16, 2017

(54) RESOLUTION ENHANCEMENT OF OCT IMAGES DURING VITREORETINAL SURGERY

(71) Applicant: NOVARTIS AG, Basel (CH)

(72) Inventor: Steven T. Charles, Memphis, TN (US)

(73) Assignee: Novartis AG, Basel (CH)

( * ) Notice: Subject to any disclaimer, the term of this patent is extended or adjusted under 35 U.S.C. 154(b) by 1 day.

(21) Appl. No.: 14/942,801

(22) Filed: Nov. 16, 2015

(51) Int. Cl.
*A61B 3/14* (2006.01)
*A61B 3/00* (2006.01)
*A61B 90/00* (2016.01)
*A61B 3/13* (2006.01)
*A61B 3/10* (2006.01)

(52) U.S. Cl.
CPC .......... *A61B 3/0025* (2013.01); *A61B 3/0041* (2013.01); *A61B 3/102* (2013.01); *A61B 3/13* (2013.01); *A61B 3/145* (2013.01); *A61B 90/37* (2016.02); *A61B 2090/3735* (2016.02)

(58) Field of Classification Search
USPC .................................. 351/206, 246
See application file for complete search history.

(56) References Cited

PUBLICATIONS

Zeiss Rescan 700 product page, downloaded Apr. 22, 2016 from http://www.zeiss.com/meditec/en_us/products---solutions/ophthalmology-optometry/glaucoma/therapy/surgical-microscopes/opmi-lumera-700.html; 3 pages, Apr. 22, 2016.

Haag-Streit Surical iOCT product page, downloaded Apr. 22, 2016 from http://www.haag-strcit-surgical.com/products/ophthalmology/toctr.html; 3 pages, Apr. 22, 2016.

Bioptigen Envisu C-Class Systems product page, downloaded Apr. 22, 2016 from http://www.leica-microsystems.com/products/optical-coherence-tomography-oct/details/product/envisu-c-class/; 5 pages, Apr. 22, 2016.

*Primary Examiner* — Jack Dinh
(74) *Attorney, Agent, or Firm* — Baker Botts L.L.P.

(57) ABSTRACT

Resolution enhancement of OCT images during ophthalmic surgery may be performed with an OCT scanning controller that interfaces to an OCT scanner used with a surgical microscope. Real-time OCT images may be acquired by the OCT scanner, while previously acquired high resolution OCT images are accessed by the OCT scanning controller. The high resolution OCT images may be morphed based on the real-time OCT images to match a deformation of the eye. The morphed high resolution OCT images may be displayed during surgery.

12 Claims, 3 Drawing Sheets

US 9,649,021 B1

RESOLUTION ENHANCEMENT OF OCT IMAGES DURING VITREORETINAL SURGERY

BACKGROUND

Field of the Disclosure

The present disclosure relates to ophthalmic surgery, and more specifically, to resolution enhancement of optical coherence tomography (OCT) images during vitreoretinal surgery.

Description of the Related Art

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The surgical microscope provides imaging and optionally illumination of the fundus during vitreoretinal surgery. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus.

In addition to viewing the fundus, surgical microscopes may be equipped with optical coherence tomography (OCT) scanners to provide additional information about portions of eye tissue involved with the vitreoretinal surgery. The OCT scanner may enable imaging below a visible surface of the eye tissue during vitreoretinal surgery. However, real-time imaging using an OCT scanner may be limited to lower resolution images.

SUMMARY

In one aspect, a disclosed method is for performing ophthalmic surgery using resolution enhancement of OCT images. The method may include viewing an interior portion of an eye of a patient using a surgical microscope generating an optical image of the interior portion of the eye, and sending a command to an OCT scanning controller coupled to the surgical microscope to generate first scan data from the interior portion of the eye. In the method, the OCT scanning controller may be in communication with an OCT scanner enabled for acquiring the first scan data. In the method, the OCT scanning controller may be enabled for receiving the first scan data from the OCT scanner, and accessing second scan data previously generated from the interior portion of the eye using OCT. In the method, the second scan data may have higher spatial resolution than the first scan data. The method may further include capturing a deformation of the eye by the first scan data. Based on the first scan data of the deformation, the method may still further include morphing the second scan data to correspond to the deformation to generate third scan data, and causing the third scan data to be displayed.

In any of the disclosed embodiments of the method, the third scan data may be displayed in an ocular of the surgical microscope. In any of the disclosed embodiments of the method, the third scan data may be displayed in an external display.

In any of the disclosed embodiments of the method, the first scan data may be received as a video signal. In any of the disclosed embodiments of the method, the third scan data may be displayed as a video signal.

In any of the disclosed embodiments of the method, the OCT scanning controller may be further enabled for performing a registration prior to the deformation, wherein the first scan data are compared with the second scan data, and accepting the registration when the first scan data matches the second scan data to a minimum degree.

In a further aspect, a disclosed OCT scanning controller performs resolution enhancement of OCT images during ophthalmic surgery. The OCT scanning controller may include a processor having access to memory media storing instructions executable by the processor for receiving a first command to generate first scan data from an interior portion of an eye of a patient, sending a second command to an OCT scanner to acquire the first scan data via a surgical microscope, and receiving the first scan data from the OCT scanner. The OCT scanning controller may further include instructions for accessing second scan data previously generated from the interior portion of the eye using OCT. In the OCT scanning controller, the second scan data may have higher spatial resolution than the first scan data. Based on the first scan data, the OCT scanning controller may further include instructions for morphing the second scan data to correspond to a deformation of the eye captured by the first scan data to generate third scan data, and causing the third scan data to be displayed.

In any of the disclosed embodiments of the OCT scanning controller, the instructions for causing the third scan data to be displayed may include instructions for causing the third scan data to be displayed in an ocular of the surgical microscope. In any of the disclosed embodiments of the OCT scanning controller, the instructions for causing the third scan data to be displayed may include instructions for causing the third scan data to be displayed in an external display.

In any of the disclosed embodiments of the OCT scanning controller, the first scan data may be received as a video signal. In any of the disclosed embodiments of the OCT scanning controller, the third scan data may be displayed as a video signal.

In any of the disclosed embodiments, the OCT scanning controller may further include instructions for performing a registration prior to the deformation, wherein the first scan data are compared with the second scan data, and accepting the registration when the first scan data matches the second scan data to a minimum degree.

Additional disclosed embodiments include an OCT scanner, a surgical microscope, and an image processing system.

BRIEF DESCRIPTION OF THE DRAWINGS

For a more complete understanding of the present disclosure, reference is now made to the following description, taken in conjunction with the accompanying drawings, in which.

DESCRIPTION OF PARTICULAR EMBODIMENTS

Figure 1:
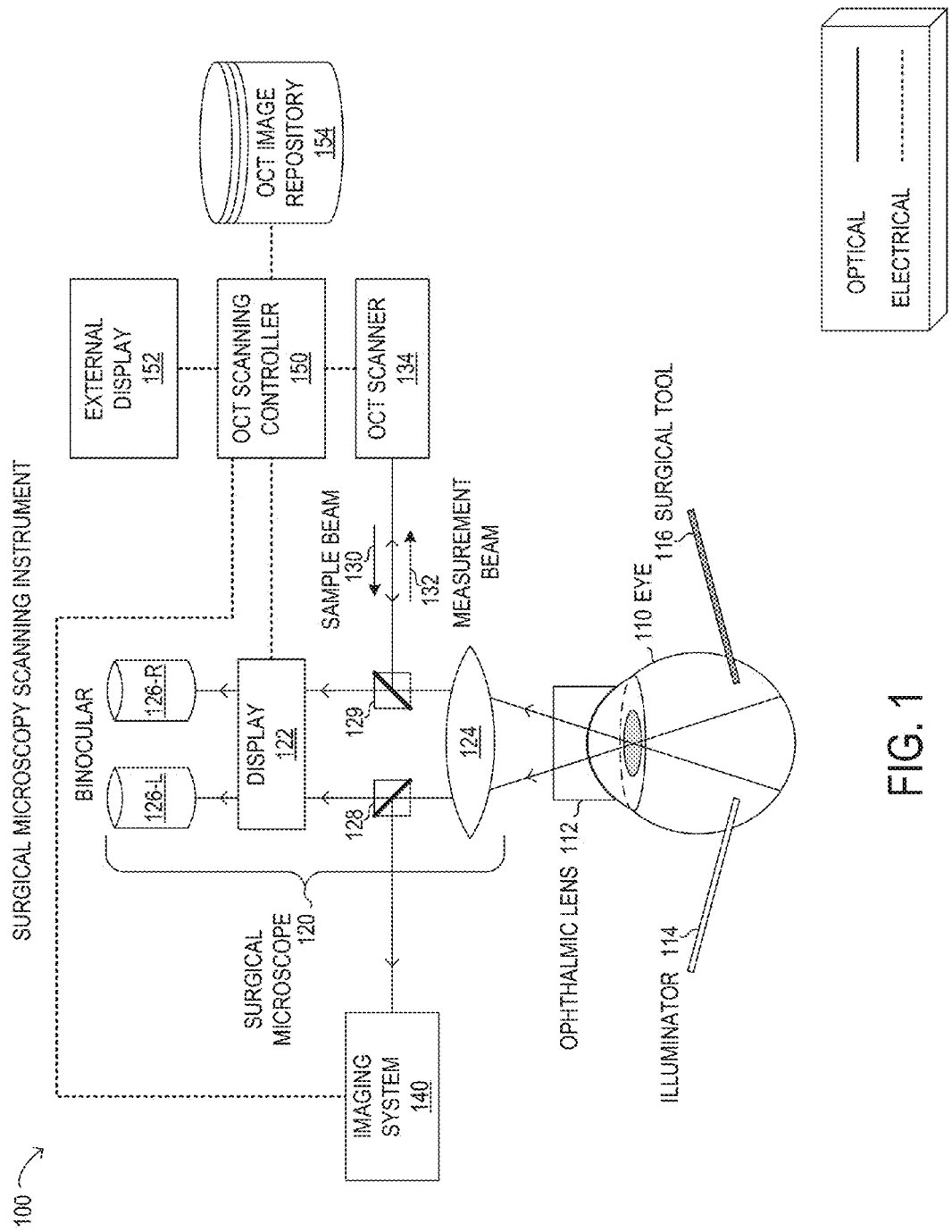
FIG. 1 is a block diagram of selected elements of an embodiment of a surgical microscopy scanning instrument.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, during vitreoretinal surgery a surgeon may view the fundus of an eye of a patient using a surgical microscope, for example, in conjunction with an ophthalmic lens for viewing through the cornea, such as a contact or non-contact lens. In order to perform any of a variety of surgical procedures, the surgeon may desire to optically scan certain portions of the fundus to generate profile depth scans of the corresponding eye tissue, such as by using an OCT scanner. The profile depth scans may reveal information about eye tissue that is not readily visible from optical images generated by the surgical microscope. The profile depth scans may be point scans (A-scan), line scans (B-scan), or area scans (C-scan). An image from a B-scan will image the depth of eye tissue along a line, while a C-scan results in 3-dimensional (3D) data that can be sectioned to provide various views, including an en face view from the optical view perspective, but which can be generated at various depths and for selected tissue layers.

Although OCT scanners have been integrated with the optics of surgical microscopes, the real-time imagery that can be provided using OCT may be limited to a lower spatial resolution than the optical images that the surgeon views intraoperatively. For example, the resolution obtained with an OCT scanner depends on the intensity of light in an OCT sample beam, as well as on a dwell time at each sampling location to acquire a sufficient amount of OCT measurement beam photons. Because the intensity of light entering the eye is limited for safety reasons to a Maximum Permissible Exposure (MPE) limit to prevent biological damage, the operational parameters for OCT to generate high resolution images may involve relatively long sampling times and may be unsuitable to perform in real-time, such as to generate a video signal that can be viewed intraoperatively. As a result, when a surgeon views real-time OCT images captured during vitreoretinal surgery, the real-time OCT images may have a substantially lower resolution than the optical images concurrently viewed by the surgeon, which may be undesirable.

The present disclosure relates to resolution enhancement of OCT images during vitreoretinal surgery. The methods and systems for resolution enhancement of OCT images during vitreoretinal surgery disclosed herein may enable the surgeon to intraoperatively view high resolution OCT images along with the optical images generated by the surgical microscope. The methods and systems for resolution enhancement of OCT images during vitreoretinal surgery disclosed herein may enable registration of real-time OCT images to match with previously acquired high-resolution OCT images. The methods and systems for resolution enhancement of OCT images during vitreoretinal surgery disclosed herein may enable an intraoperative deformation of the eye to be viewed with high resolution. The methods and systems for resolution enhancement of OCT images during vitreoretinal surgery disclosed herein may further enable the field of view to be output to an external display.

As will be described in further detail, resolution enhancement of OCT images during vitreoretinal surgery disclosed herein is performed using an OCT scanning controller that is integrated with the OCT scanner and the surgical microscope. The OCT scanning controller may send commands to control operation of the OCT scanner, including for positioning as indicated by a user, typically the surgeon. The OCT scanning controller may receive user input and may communicate with the OCT scanner to acquire first scan data that is collected in real-time. The OCT scanning controller may access second scan data previously generated for the patient using OCT and having higher spatial resolution than the first scan data.

Referring now to the drawings, FIG. 1 is a block diagram showing a surgical microscopy scanning instrument 100. Instrument 100 is not drawn to scale but is a schematic representation. As will be described in further detail, instrument 100 may be used during vitreoretinal surgery to view and analyze a human eye 110. As shown, instrument 100 includes surgical microscope 120, OCT scanning controller 150, external display 152, OCT image repository 154, and OCT scanner 134. Also shown in FIG. 1 are imaging system 140, ophthalmic lens 112, as well as surgical tool 116 and illuminator 114.

As shown, surgical microscope 120 is depicted in schematic form to illustrate optical functionality. It will be understood that surgical microscope 120 may include various other electronic and mechanical components, in different embodiments. Accordingly, objective 124 may represent a selectable objective to provide a desired magnification or field of view of the fundus of eye 110. Objective 124 may receive light from the fundus of eye 110 via ophthalmic lens 112 that rests on a cornea of eye 110. It is noted that various types of ophthalmic lenses 112 may be used with surgical microscope 120, including contact lenses and non-contact lenses. To perform vitreoretinal surgery, various tools and instruments may be used, including tools that penetrate the sclera, represented by surgical tool 116. Illuminator 114 may be a special tool that provides a light source from within the fundus of eye 110.

In FIG. 1, surgical microscope 120 is shown with a binocular arrangement with two distinct but substantially equal light paths that enable viewing with binoculars 126 that comprise a left ocular 126-L and a right ocular 126-R. From objective 124, a left light beam may be split at beam splitter 128, from where imaging system 140 and left ocular 126-L receive the optical image. Also from objective 124, a right light beam may be split at partial mirror 129, which also receives sample beam 130 from OCT scanner 134, and outputs measurement beam 132 to OCT scanner 134. Partial mirror 129 also directs a portion of the right light beam to right ocular 126-R. Display 122 may represent an optoelectronic component, such as an image processing system that receives the data from OCT scanning controller 150 and generates image output for left ocular 126-L and right ocular 126-R, respectively. In some embodiments, display 122 includes miniature display devices that output images to binoculars 126 for viewing by the user. It is noted that the optical arrangement depicted in FIG. 1 is exemplary and may be implemented differently in other embodiments.

In FIG. 1, OCT scanning controller 150 may have an electrical interface with display 122, for example, for outputting display data. In this manner, OCT scanning controller 150 may output a display image to display 122 that is viewed at binoculars 126. Because the electrical interface between imaging system 140 and OCT scanning controller 150 may support digital image data, OCT scanning controller 150 may perform image processing in real-time with relatively high frame refresh rates, such that a user of surgical microscope 120 may experience substantially instantaneous feedback to user input for controlling the selected portion of eye 110 for scanning, as well as other operations. External display 152 may output similar images as display 122, but may represent a stand-alone monitor for viewing by various personnel during vitreoretinal surgery. Display 122 or external display 152 may be implemented as a liquid crystal display screen, a computer monitor, a television or the like. Display 122 or external display 152 may comply with a display standard for the corresponding type of display, such as video graphics array (VGA), extended graphics array (XGA), digital visual interface (DVI), high-definition multimedia interface (HDMI), etc.

With the binocular arrangement of surgical microscope 120 in FIG. 1, imaging system 140 may receive a portion of the left light beam that enables imaging system 140 to independently process, display, store, and otherwise manipulate light beams and image data. Accordingly, imaging system 140 may represent any of a variety of different kinds of imaging systems, as desired.

As shown, OCT scanner 134 may represent an embodiment of various kinds of OCT scanners. It is noted that other types of optical scanners may be used with the arrangement depicted in FIG. 1. OCT scanner 134 may control output of sample beam 130 and may receive measurement beam 132 that is reflected back in response to photons of sample beam 130 interacting with tissue in eye 110. OCT scanner 134 may also be enabled to move sample beam 130 to the selected location indicated by the user. OCT scanning controller 150 may interface with OCT scanner 134, for example, to send commands to OCT scanner 134 indicating the selected location to generate scan data, and to receive the scan data acquired by OCT scanner 134. It is noted that OCT scanner 134 may represent various types of OCT instruments and configurations, as desired, such as but not limited to time domain OCT (TD-OCT) and frequency domain OCT (FD-OCT). In particular, the scan data generated by OCT scanner 134 may include two-dimensional (2D) scan data of a line scan and three-dimensional (3D) scan data for an area scan. The scan data may represent a depth profile of the scanned tissue that enables imaging below a visible surface within the fundus of eye 110.

As shown, OCT image repository 154 represents a digital storage medium, such as a database or a file system and corresponding storage devices, that provides access to OCT images. Specifically, high-resolution OCT images of eye 110 may be recorded in advance of the vitreoretinal surgery and stored in OCT image repository 154, such that OCT scanning controller 150 can access the high-resolution OCT images.

In operation of instrument 100, the user may view the fundus of eye 110 using binoculars while vitreoretinal surgery is performed on eye 110. The user may provide user input to OCT scanning controller to initiate an OCT scan. OCT scanning controller may, in turn, communicate with OCT scanner 134 to control scanning operations and perform a real-time OCT scan to generate first scan data. However, the first scan data generated by OCT scanner 134 intraoperatively may be of low resolution, as discussed previously. Therefore, instead of displaying the first scan data at display 122, OCT scanning controller 150 may access second scan data from OCT image repository 154, the second scan data comprising high resolution OCT images of eye 110 of the patient. Then, OCT scanning controller 150 may internally modify the second scan data to match a deformation detected in the first scan data, such as an interoperative deformation of the sclera caused by surgical tool 116. Then, OCT scanning controller 150 may display third scan data (comprising the modified second scan data) to the user such that a high-resolution OCT image is viewed at binoculars 126. The processing by OCT scanning controller 150 may be performed in real-time, for example, based on first scan data that is acquired as frames of a video signal, with frame rates of multiple frames per second or higher, to generate corresponding frames of the third scan data as a video signal.

Modifications, additions, or omissions may be made to surgical microscopy scanning instrument 100 without departing from the scope of the disclosure. The components and elements of surgical microscopy scanning instrument 100, as described herein, may be integrated or separated according to particular applications. Surgical microscopy scanning instrument 100 may be implemented using more, fewer, or different components in some embodiments.

Figure 2:
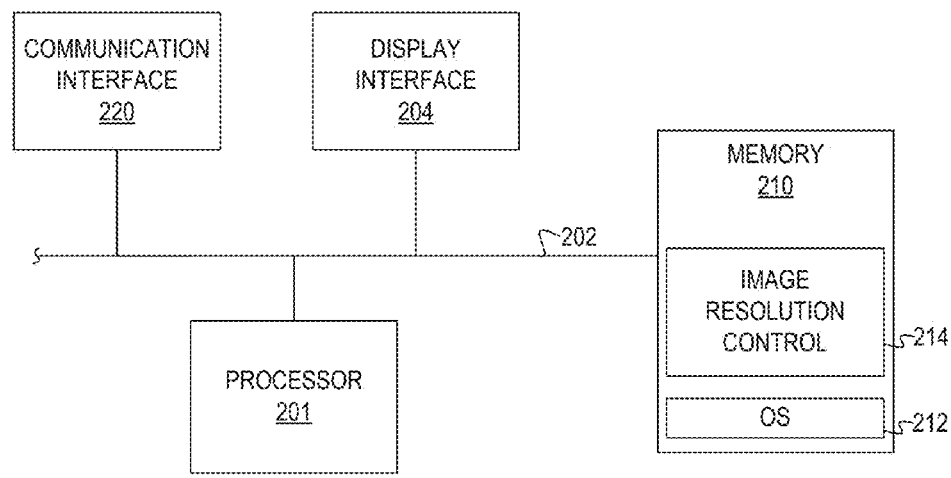
FIG. 2 is a block diagram of selected elements of an embodiment of a scanning controller.

Referring now to FIG. 2, a block diagram illustrating selected elements of an embodiment of OCT scanning controller 150, described above with respect to FIG. 1, is presented. In the embodiment depicted in FIG. 2, OCT scanning controller 150 includes processor 201 coupled via shared bus 202 to memory media collectively identified as memory 210.

OCT scanning controller 150, as depicted in FIG. 2, further includes communication interface 220 that can interface OCT scanning controller 150 to various external entities, such as OCT scanner 134 or imaging system 140, among other devices. In some embodiments, communication interface 220 is operable to enable OCT scanning controller 150 to connect to a network (not shown in FIG. 2). In embodiments suitable for resolution enhancement of OCT images during vitreoretinal surgery, OCT scanning controller 150, as depicted in FIG. 2, includes display interface 204 that connects shared bus 202, or another bus, with an output port for one or more displays, such as display 122 or external display 152.

In FIG. 2, memory 210 encompasses persistent and volatile media, fixed and removable media, and magnetic and semiconductor media. Memory 210 is operable to store instructions, data, or both. Memory 210 as shown includes sets or sequences of instructions, namely, an operating system 212, and an image resolution control application 214. Operating system 212 may be a UNIX or UNIX-like operating system, a Windows® family operating system, or another suitable operating system.

Figure 3:
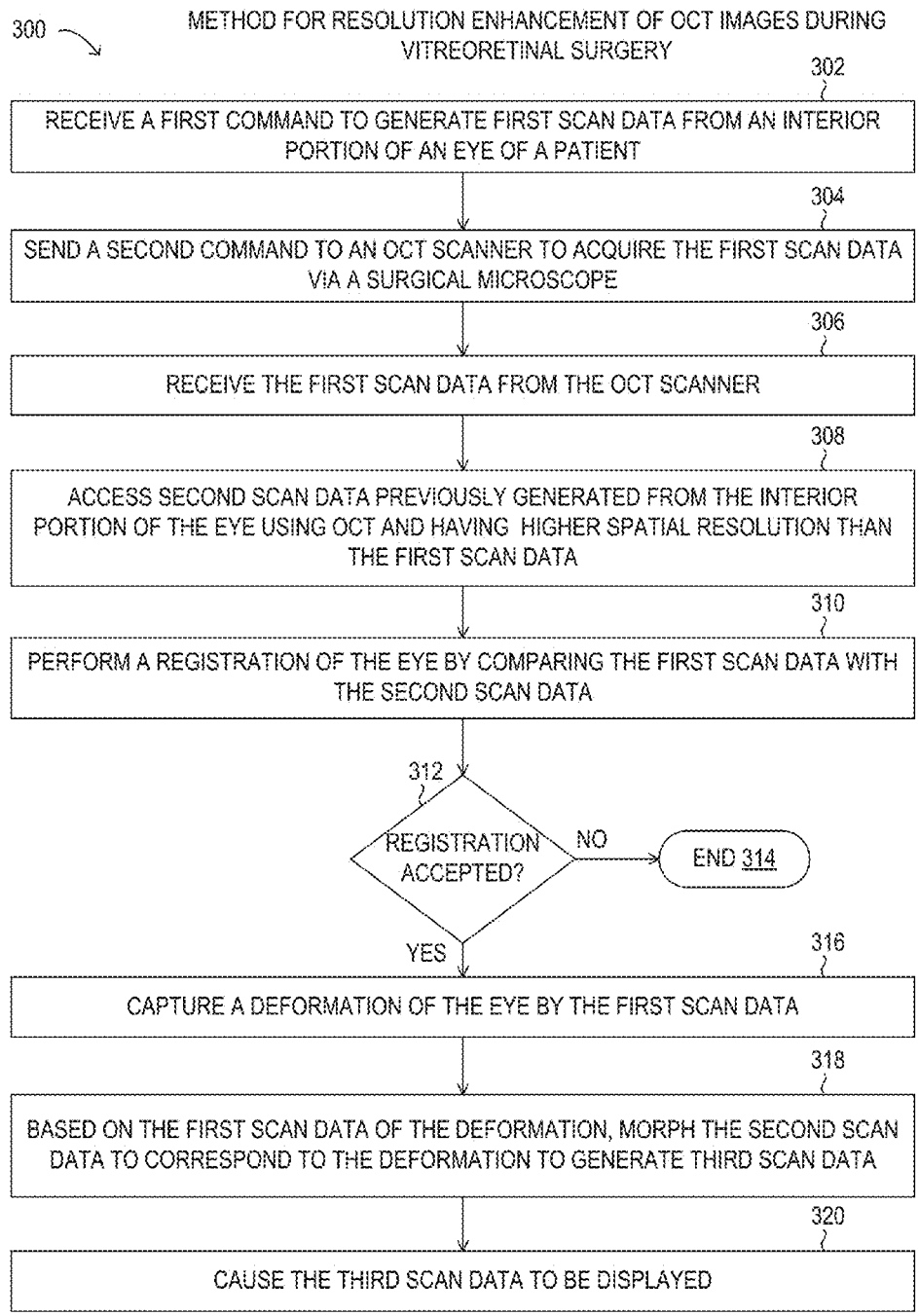
FIG. 3 is a flow chart of selected elements of a method for resolution enhancement of OCT images during vitreoretinal surgery.

Referring now to FIG. 3, a flow chart of selected elements of an embodiment of a method 300 for resolution enhancement of OCT images during vitreoretinal surgery, as described herein, is depicted. Method 300 describes steps and procedures that may be performed while surgical microscopy scanning instrument 100 is operated to view the fundus of an eye and perform surgical procedures based on the view of the fundus. Accordingly, at least certain portions of method 300 may be performed by image resolution control application 214. It is noted that certain operations described in method 300 may be optional or may be rearranged in different embodiments. Method 300 may be performed by image resolution control application 214 to interact with a surgeon or other medical personnel, referred to herein as a "user".

Prior to method 300, it may be assumed that surgical microscopy scanning instrument 100 is being used to view an interior portion of an eye of a patient, such as described in FIG. 1. Then, method 300 may begin, at step 302, by receiving a first command to generate first scan data from an interior portion of an eye of a patient. The first scan data are C-scans (volumetric scans) of the interior portion of the eye. At step 304, a second command may be sent to an OCT scanner to acquire the first scan data via the surgical microscope. At step 306, the first scan data may be received from the OCT scanner. It is noted that the first scan data may be continuously acquired and received, such that steps 304 and 306 represent initiation of continuous operations to acquire and receive the first scan data. At step 308, second scan data previously generated from the interior portion of the eye using OCT and having higher spatial resolution than the first scan data may be accessed. The second scan data are also C-scans (volumetric scans) of the interior portion of the eye. At step 310, a registration of the eye may be performed by comparing the first scan data with the second scan data. In some embodiments, the registration at step 310 may include displaying the first scan data and the second scan data to the user and obtaining confirmation from the user. At step 312, a decision may be made whether the registration performed at step 310 is accepted.

Acceptance of the registration may be based on a degree of spatial matching between the first scan data and the second scan data. As noted, the user may be relied upon to confirm the degree of spatial matching and accept the registration. In some embodiments, an automatic procedure may be used for registration. For example, the second scan data may be downsampled to match a resolution of the first scan data and then the downsampled second scan data may be compared with the first scan data for differences. The differences may be quantified using certain criteria, such as less than 5% difference, or 1-5% difference, or less than 1% difference, in different examples. Additionally, further operations such as orientation and scaling of imaged values may be performed on the second scan data during registration. In order to align the first scan data and the second scan data, certain specific features (such as tissues, layers, blood vessels, structures, etc.) may be identified during the registration in step 310. In particular embodiments, OCT angiography using auto-segmentation of retinal blood vessels is used to guide alignment in step 310 of the second scan data with the first scan data. In some embodiments, the internal limiting membrane (ILM) or a back surface of a detached retina may be used to guide alignment in step 310. Acceptance of the registration may indicate that the second scan data are valid for the eye and correspond to the first scan data.

When the result of step 312 is NO and the registration is not accepted, method 300 may end at step 314. When the result of step 312 is YES and the registration is accepted, method 300 may proceed to step 316, where a deformation of the eye is captured by the first scan data. As noted above, the first scan data may be continuously acquired and received as a result of steps 304 and 306. In some embodiments, the first scan data are continually overwritten by refreshing as new OCT scans are performed in real-time. The deformation of the eye at step 316 may be the result of an intraoperative procedure by the surgeon.

At step 318, based on the first scan data of the deformation, the second scan data may be morphed to correspond to the deformation to generate third scan data. The morphing may be performed with various image processing algorithms. For example, certain specific features (such as tissues, layers, blood vessels, structures, etc.) may be identified from the registration and may be subsequently mapped from the first scan data to the second scan data to represent the deformation in step 318. In particular embodiments, OCT angiography using auto-segmentation of retinal blood vessels is used to guide alignment and morphing in step 318 of the second scan data to match the first scan data. In some embodiments, the internal limiting membrane (ILM) or a back surface of a detached retina may be used to guide alignment and morphing in step 318. Additionally, it is noted that the morphing operation in step 318 is dependent on a number of variables and factors associated with instrument 100. For example, the morphing is dependent on a microscope magnification or selection of a given objective 124, as well as on a type of ophthalmic lens 112 used. The morphing may also be dependent on a distance between an optical element, such as a non-contact lens used for ophthalmic lens 112, and the eye. Thus, upon a change in such operative variables, at least step 318 in method 300 may be repeated to refresh the third scan data. At step 320, the third scan data may be caused to be displayed. The third scan data may be displayed at binoculars 126 or at external display 152 or both. It is noted that the third scan data are displayed in addition to the optical image provided by the surgical microscope that is a live optical view of the interior portion of the eye.

As disclosed herein, resolution enhancement of OCT images during ophthalmic surgery may be performed with an OCT scanning controller that interfaces to an OCT scanner used with a surgical microscope. Real-time OCT images may be acquired by the OCT scanner, while previously acquired high resolution OCT images are accessed by the OCT scanning controller. The high resolution OCT images may be morphed based on the real-time OCT images to match a deformation of the eye. The morphed high resolution OCT images may be displayed during surgery.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for performing ophthalmic surgery, the method comprising:
    viewing an interior portion of an eye of a patient using a surgical microscope generating an optical image of the interior portion of the eye; and sending a command to an optical coherence tomography (OCT) scanning controller coupled to the surgical microscope to generate first scan data from the interior portion of the eye, wherein the OCT scanning controller is in communication with an OCT scanner enabled for acquiring the first scan data, wherein the OCT scanning controller is enabled for, receiving the first scan data from the OCT scanner;

accessing second scan data previously generated from the interior portion of the eye using OCT, wherein the second scan data has higher spatial resolution than the first scan data;

capturing a deformation of the eye by the first scan data;

based on the first scan data of the deformation, morphing the second scan data to correspond to the deformation to generate third scan data; and causing the third scan data to be displayed.

2. The method of claim 1, wherein the third scan data are displayed in an ocular of the surgical microscope.

3. The method of claim 1, wherein the third scan data are displayed in an external display.

4. The method of claim 1, wherein the first scan data are received as a video signal.

5. The method of claim 1, wherein the third scan data are displayed as a video signal.

6. The method of claim 1, wherein the OCT scanning controller is further enabled for:

performing a registration prior to the deformation, wherein the first scan data are compared with the second scan data; and accepting the registration when the first scan data matches the second scan data to a minimum degree.

7. An optical coherence tomography (OCT) scanning controller to perform resolution enhancement of OCT images during ophthalmic surgery, the OCT scanning controller further comprising:

a processor having access to memory media storing instructions executable by the processor for, receiving a first command to generate first scan data from an interior portion of an eye of a patient;

sending a second command to an OCT scanner to acquire the first scan data via a surgical microscope;

receiving the first scan data from the OCT scanner;

accessing second scan data previously generated from the interior portion of the eye using OCT, wherein the second scan data has higher spatial resolution than the first scan data;

based on the first scan data, morphing the second scan data to correspond to a deformation of the eye captured by the first scan data to generate third scan data; and causing the third scan data to be displayed.

8. The OCT scanning controller of claim 7, wherein the instructions for causing the third scan data to be displayed include instructions for causing the third scan data to be displayed in an ocular of the surgical microscope.

9. The OCT scanning controller of claim 7, wherein the instructions for causing the third scan data to be displayed include instructions for causing the third scan data to be displayed in an external display.

10. The OCT scanning controller of claim 7, wherein the first scan data are received as a video signal.

11. The OCT scanning controller of claim 7, wherein the third scan data are displayed as a video signal.

12. The OCT scanning controller of claim 7, further comprising instructions for:

performing a registration prior to the deformation, wherein the first scan data are compared with the second scan data; and accepting the registration when the first scan data matches the second scan data to a minimum degree.

* * * * *